United States Patent [19]
Shlyankevich

[11] Patent Number: 5,569,459
[45] Date of Patent: Oct. 29, 1996

[54] PHARMACEUTICAL COMPOSITIONS FOR THE MANAGEMENT OF PREMENSTRUAL SYNDROME AND ALLEVIATION OF MENOPAUSAL DISORDERS

[75] Inventor: Mark Shlyankevich, Waterbury, Conn.

[73] Assignee: Bio-Virus Research Incorporated, San Mateo, Calif.

[21] Appl. No.: 389,007

[22] Filed: Feb. 15, 1995

[51] Int. Cl.⁶ ................................................ A61K 35/78
[52] U.S. Cl. ..................... 424/195.1; 514/456; 514/874
[58] Field of Search ................... 424/195.1; 514/456, 514/874

[56] References Cited

U.S. PATENT DOCUMENTS

| | | | |
|---|---|---|---|
| 4,428,876 | 1/1984 | Iwamura . | |
| 4,549,990 | 10/1985 | Seguin et al. . | |
| 5,352,384 | 10/1994 | Shen | 252/398 |
| 5,424,331 | 6/1995 | Shlyankevich | 514/456 |
| 5,462,949 | 10/1995 | Jones | 514/324 |
| 5,462,950 | 10/1995 | Fontana | 514/324 |

OTHER PUBLICATIONS

D. P. Rose, Nutrition 8:47–51, 1992.
P. E. Belchetz, Practitioner, 234:491–493, 1990.
Taylor, Neuropsychobiology 12:16, 1984.
Brit, Med Bull. 48:356, 1992.

Primary Examiner—John W. Rollins
Attorney, Agent, or Firm—Herbert Dubno; Jonathan Myers

[57] ABSTRACT

A composition is disclosed for controlling the stimulation of estrogen production, which comprises:

(a) 15 to 120 parts by weight of one or more phytoestrogen compounds calculated as a free aglycon form of isoflavone;

(b) up to 75 parts by weight of dried licorice root extract;

(c) 10 to 80 parts by weight of a sedative selected from the group consisting of Valerian root dry extract, passion flower dry extract, and Ginseng root powder;

(d) up to 50, preferably 10 to 20 parts by weight of beta-carotene;

(e) up to 200, preferably 15 to 150 parts by weight of pyridoxine hydrochloride;

(f) up to 50, preferably 12 to 30 parts by weight of Vitamin E;

(g) up to 600, preferably 100 to 450 parts by weight of calcium contained in a biologically acceptable calcium salt;

(h) up to 200, preferably 150 to 250 parts by weight of magnesium contained in a biologically acceptable magnesium salt;

(i) up to 100, preferably 10 to 50 parts by weight of zinc contained in a biologically acceptable zinc salt;

(j) up to 30 parts by weight of coumestan; and (k) up to 50 parts by weight of pantothenic acid; in admixture with a biologically acceptable inert carrier.

10 Claims, No Drawings

PHARMACEUTICAL COMPOSITIONS FOR THE MANAGEMENT OF PREMENSTRUAL SYNDROME AND ALLEVIATION OF MENOPAUSAL DISORDERS

FIELD OF THE INVENTION

This invention relates to new pharmaceutical compositions that can be used as dietary supplements for the management of premenstrual syndrome and for alleviation of menopausal disorders and for control of stimulating estrogen production in a prepubescent female. More particularly, the invention relates to such pharmaceutical compositions and dietary supplements that contain natural soybean phytoestrogens of the isoflavone group.

BACKGROUND OF THE INVENTION

There are numerous chronic diseases that are a function of altered hormonal status, especially the sex hormones. The most dominant of all of the female hormones are the estrogens which control the reproductive system as well as the function of many other cells and tissues, including bones, as well as the cardiovascular and immune systems, angiogenesis, brain and nerves, and lipid metabolism, etc.

Phytoestrogens and their metabolites (equol, etc.) possess weak estrogenic activity and compete for estrogen receptors in target tissues, including the central nervous system (hypothalamus/pituitary), uterus, breast cells, osteoblasts/osteoclasts, etc. Despite this weak intrinsic estrogenicity, the phytoestrogens may actually exert an attenuating antiestrogenic effect. See Rose, D. P., Nutrition, 8:47 to 51 (1992).

The basic factors controlling female ovarian functions are the anterior pituitary gonadotropins: follicle-stimulating hormone (FSH), which directs follicle and ovum development, and lutenizing hormone (LH) that induces estrogen secretion. The hypothalamus controls the pituitary function by means of secreting pulsatile gonadotropin releasing hormone (GnRH) production. There is a strong negative feedback inhibition of hypothalamus/pituitary function that is conducted by estrogen and inhibin (the latter is a glycoprotein that selectively inhibits FSH secretion). See Belchetz, P. E., Practitioner, 234:491 to 493 (1990).

In puberty the hypothalamic GnRH secretion is raised and this induces estrogen production through pituitary LH. Menarche, the first menstrual period, is delayed for about one to one and one half years, and the early menstrual cycles are usually not accompanied by ovulation, which may be delayed for one to one and one half years. During this overall time of 2 to 3 years there is no established feedback mechanism, either positive or negative. As a result hormonal imbalances are induced and a number of physical and psychological disorders manifest themselves.

Premenstrual tension is exhibited by a series of symptoms which occur during the second, luteal phase of the menstrual cycle. Premenstrual tension is induced by a surge of estrogen that arises because the negative feedback inhibition is altered.

Premenstrual syndrome (PMS) or premenstrual tension is a disorder that affects menstruating women one to two weeks before menses begins. The pathophysiologic mechanisms of PMS are weakly understood. One of the causes is a hormonal imbalance, an excessive estrogen level and an inadequate progesterone level. Estrogen levels in the blood and hypothalamus increase at the end of the first part of the menstrual cycle (the follicular phase); the second peak comes a week before a menstrual flow (the luteal phase). It is the second estrogen peak, which coincides with the progesterone peak, that determines the extent of the PMS.

Beside the elevated level of estrogen circulating in the blood, some PMS manifestations, such as mood or behavior, are induced by a drop in the level of biogenic amines in the central nervous system. Lower brain neurotransmitters, such as serotonin and dopamine, have been implicated in the etiology of PMS. See Taylor, D. L. et al, Neuropsychobiology, 12:16 (1984) and Kuchel, O. et al, Contrib. Nephrol., 13:27 (1978). For example it was found that 40% of depressed patients with a lower level of 5-hydroxyindoleacetic acid, the breakdown product of serotonin, had attempted suicide. See Asberg, M. New York Academy of Sciences, 1:1 (1986). Vitamin B6 is thought to be unique in its ability to normalize the metabolism of biogenic amines by increasing the activity of various pyridoxal phosphate dependent enzymatic reactions. See Berman, M. K. et al, J. Amer. Diet. Assoc., 90:859 to 861 (1990).

Another basis for implicating lower brain neurotransmitters, such as dopamine, in the etiology of PMS is chronic magnesium deficiency. See Abraham, G. E. et al, Am. J. Clin. Nutr. 34:2364. Calcium and dairy products interfere with magnesium absorption, and refined sugar increases the urinary excretion of magnesium. It was found that patients with severe PMS symptoms, such as premenstrual anxiety, irritability and nervous tension consumed five-fold more dairy products, and three-fold more refined sugar than those affected patients without these specific symptoms. See Chuong, C. J. et al, Clin. Obst. Gynecol., 35:679 to 692 (1992). Aggressive behavior in girls consuming excess dairy products, including calcium, has also been observed. On the other hand, estrogen can enhance magnesium utilization, but an estrogen-induced shift of magnesium can be deleterious when the estrogen level is high and magnesium intake is less than optimal. See Seeling, M. S., J. Am. Coll. Nutr., 12:442 to 458 (1993).

The clinical diagnosis of PMS involves a combination of physical and behavioral symptoms including headache, breast tenderness, swelling of extremities, tension, anxiety and mood swings. It is possible to differentiate women with three premenstrual symptom severity patterns: premenstrual syndrome (PMS) proper, premenstrual magnification (PMM), and low symptom (LS). See Mitchell, E. S., Nursing Res., 43:25 to 30 (1994). The incidence of premenstrual tension in gynecologic practice is estimated at 50%, but studies say that only about 2% of women actually suffer from PMS and require extensive medical treatment. See Hargrove, J. T. et al, J. Reprod. Med., 27:721 to 724 (1982). The other patients could be supported merely by diet and dietary supplements.

An ideal therapy for PMS has not been realized. The nutritional factors in pathophysiology and treatment of PMS are widely discussed, but there is no general agreement on the nutritional program best suited to treat PMS. Most American physicians recommend dietary changes in additional to nutritional supplements in management of such patients. See Lyon, K. E. et al, J. Reprod. Med., 29:705 to 711 (1984).

The limited consumption of refined sugar, salt, red meat, animal fat, alcohol, coffee, tea, chocolate, and dairy products combined with increased intake of fish, poultry, whole grains, legumes, complex carbohydrates, green leafy vegetables, cereals, and cis-linoleic acid-containing foods is a diet generally recommended to PMS sufferers. See Chuong, C. J. et al, Clin. Obst. Gynec., 35:679 to 692 (1992).

Several of these approaches to controlling PMS promote a decrease in endogenous estrogen production, and its inactivation and excretion. Indeed, the restriction of animal fat decreases cholesterol intake, and the latter is a common precursor of steroid hormones: androgens and estrogens. Leguminous seeds containing phytoestrols and saponins are potential hypocholesterolemic agents. See Ikeda I. et al, Biochem. Biophys. Acta.732:651 to 658 (1983). Whole grains, cereals, green vegetables (indole-3-carbinol), and complex carbohydrates could be effective for the conversion of estrogens into inactive metabolites. Dietary fiber significantly moves the estrogen balance into inactive forms by means of alteration of intestinal metabolism, and reduction of steroid reabsorption. See Adlercreutz, H. et al, J. Steroid Biochem., 24:289 to 296 (1986).

The beneficial effects on PMS have been shown for Vitamins A, B6 and E as well as for the minerals zinc and magnesium in several studies. See Chuong, C. J. et al, Clin. Obst. Gynec., 35:679 to 692 (1992). Multiple vitamin and mineral supplements, including their megadoses, recently have been used for the treatment of PMS. The nutritional supplement Optivite® (Optimox Corp., Torrance, Calif.) was especially formulated to provide proper nutrition for women with PMS.

Unfortunately the known effects of dietary management of PMS, including vitamin and mineral supplements, have not been clearly established, and so up to now diet management can serve only as an auxiliary treatment. There are no data about using soyfood or soy isoflavones for treatment of PMS. It was shown in a human study that consumption of 60 g of soy protein per day (containing about 60 to 80 mg of isoflavones) leads to significant changes in the menstrual cycle, with prolongation of cycle length, especially the first, follicular phase. These physiological effects are beneficial with regard to risk factors for breast and ovarian cancer, and do not prevent a pregnancy. See Setcheil, K., Role of Soy in Prevention and Treating Chronic Disease, The First Int. Symp., Mesa, Ariz. (1994). Native Chinese and Japanese women have a delayed menarche, and this effect can be explained by dietary factors, especially by the high consumption of soy food. See Yuam, J. M. et al, Cancer Res., 48:1949 (1988).

Following menopause, women become deficient in estrogen production and the negative feedback inhibition is slackened. As a direct result the activity of the hypothalamus/pituitary is enhanced. The hypothalamus is strained and influences vasomotor and thermoregulatory centers and induces hot flashes, sweats, and other symptoms of discomfort relative to climate.

Menopause is the transition from the reproductive to the non-reproductive stage of a woman's life, and it is characterized by cessation of menstruation. However, menopause has come to signify much more than simply the loss of reproductive capability, and has been associated with a number of acute and chronic conditions.

In the perimenopausal period, a complex of climacteric symptoms appears, but menstruating still continues. The early postmenopausal period is characterized by gradual cessation of climacteric symptoms. These symptoms may persist for five years or longer in 25% of the female population and may even be lifelong in a small minority.

The consequences of menopause are highly controversial and pose an important public health issue. The vasomotor climacteric symptoms (EG). (e.g. hot flashes, sweats, headaches) may be caused by an estrogen deficiency, and supplemented by a large variety of "atypical" physical and mental complaints (e.g. feeling ill at ease, tiredness, depression, sexual problems). Unfortunately for some women, the frequency of flashes is so high that life itself can be dominated by them.

The pathogenesis of menopausal symptoms is not well known. Estrogen deficiency causes two types of symptoms: those attributable to vasomotor disturbances (and secondary effects such as insomnia) and those attributable to genital atrophy. Vasomotor symptoms affect 75% of postmenopausal women, but only about 30% seek medical help for those symptoms. See Belchetz, P. E., New Engl. J. Med., 330:1062 to 1071 (1994). The alteration of negative feedback inhibition plays a key role in menopausal disorders (see above). Hormone replacement therapy (HRP) can improve the negative feedback mechanism, and decrease the level of plasma gonadotropins. See Balfour, J. A. et al, Drug, 40:561 to 582 (1990).

The beneficial effect of HRT on postmenopausal women is substantial. HRT relieves symptoms that are incontrovertibly caused by estrogen deficiency, but the response of other symptoms is less predictable. See Barlow, D. H., Brit. Med. Bull., 48:356 to 367 (1992). Many peri- and postmenopausal women have been treated with ovarian hormones in an attempt to alleviate the symptoms of menopause, and more recently in the hope of preventing osteoporosis and reducing the risk of ischemic heart disease. However, the unopposed estrogens increase the risk of endometrial and breast cancer. See Rosenberg, L. A., Am. J. Public Health, 83:1670 to 1673 (1993).

It is known that HRT by estrogens is effective to relieve the symptoms of menopause. See Brit. Med. Bull., 1992, 48:356, there is reason to expect that soybean phytoestrogens might exert a similar effect. See Dr. H. Aldercreutz et al, Lancet, 1992, 339:1233. "High Levels of Isoflavonoid Phytoestrogens may partially explain why hot flashes and other menopausal symptoms are so infrequent in Japanese women."

The non-drug treatment of menopausal symptoms includes dietary recommendations (avoid dairy and animal products), caffeine, etc.), and several nutritional supplements. These supplements include:

Vitamins: Very important vitamins include E, B5 and B6 using soy lecithin as an emulsifier for Vitamin E. Vitamin C is also helpful.

Minerals: Calcium and magnesium are important. Potassium and selenium are helpful.

Herbs Black cohosh, damiana, licorice, raspberry, sage, ginseng, dong quai, primrose oil, and blackcurrant oil.

Most of these plant products and some vitamins and minerals are used in different special menopausal formulas, which are manufactured by several producers and are available in health food stores. None of these products has proved satisfactory in the treatment of post-menopausal disorders. All of these known products merely treat symptoms and do not alleviate a hormonal deficiency. For example, it was shown that Dong quai, the dried root of Angelica sinensis in recommended doses (200 mg Rejuvex, Ginsana®) is not effective; its therapeutic dose according to Chinese medicine is 8 to 15 g per day. See Tyler, V. E., JAMA, 271:1210 (1994).

OBJECTS OF THE INVENTION

It is an object of the invention to provide a new pharmaceutical composition and a method of treatment that is highly effective in the treatment of an estrogen imbalance in females suffering from premenstrual syndrome.

It is a further object of the invention to provide a new pharmaceutical composition and a method for treating an estrogen imbalance in a prepubescent female prior to menarch.

It is yet a further object of the invention to provide a new pharmaceutical composition and a method for treating females suffering from an estrogen deficiency following menopause.

SUMMARY OF THE INVENTION

These objects are accomplished in accordance with the present invention which provides a composition for controlling the stimulation of estrogen production, which comprises:

(a) 15 to 120 parts by weight of one or more phytoestrogen compounds calculated as a free aglycon form of isoflavone;

(b) up to 75 parts by weight of dried licorice root extract;

(c) 10 to 80 parts by weight of a sedative selected from the group consisting of Valerian root dry extract, passion flower dry extract, and Ginseng root powder;

(d) up to 50, preferably 10 to 20 parts by weight of beta-carotene;

(e) up to 200, preferably 15 to 150 parts by weight of pyridoxine hydrochloride;

(f) up to 50, preferably 12 to 30 parts by weight of Vitamin E;

(g) up to 600, preferably 100 to 450 parts by weight of calcium contained in a biologically acceptable calcium salt;

(h) up to 300, preferably 150 to 250 parts by weight of magnesium contained in a biologically acceptable magnesium salt;

(i) up to 100, preferably 10 to 50 parts by weight of zinc contained in a biologically acceptable zinc salt;

(j) up to 30 parts by weight of coumestan; and (k) up to 50 parts by weight of pantothenic acid; in admixture with a biologically acceptable inert carrier.

The soybean phytoestrogen is preferably an isoflavone selected from the group consisting of genistein, daidzein, their glycosides and mixtures thereof. The main soybean isoflavones are genistein and daidzein. In raw soybeans and soy flour they are conjugated with glucose (glycosides), and are named genistin and daidzin.

The free (aglycon) and conjugated forms of isoflavones have the following molecular weights, respectively:

Genistein 270, Genistin 450;

Daidzein 254, Daidzin 434;

In the soy phytoestrogens used as ingredients in the new compositions the concentration of isoflavones is preferably about 30% by weight, and the principal form of the isoflavones will be as the abovementioned conjugates. The breakdown of conjugated isoflavones concerning isoflavone and glucose in the soy phytoestrogen are as follows:

45 mg of free isoflavones—80 mg of glycosides 60 mg of free isoflavones—105 mg of glycosides.

The preferred full weight of a pharmaceutical composition would be:

for 45 mg of free isoflavone—265 mg of composition;

for 65 mg of free isoflavone—350 mg of composition.

One kg of initial soybean concentrate would be sufficient to provide enough soybean phytoestrogens for 3000 to 3500 daily doses of the composition.

The full weight of the entire daily dose of the composition is preferably 1,160 to 1,285 mg, which should preferably be divided into two capsules, tablets or other forma that are easily orally administered. If preferred, this same total daily dosage may be divided into three or even four doses per day.

The pharmaceutical compositions according to the present invention may include up to 75 parts by weight of dried licorice root extract per 15 to 120 parts by weight of the soy phytoestrogens. When the dried licorice root extract is employed in the pharmaceutical compositions, the preferred range is 50 to 75 parts by weight.

The preferred concentrations of the sedatives employed include 45 parts of the passion flower dried extract, 60 parts of the Valerian root dry extract, or 10 parts by weight of the Ginseng root powder per 15 to 120 parts by weight of the soy phytoestrogens.

The compositions may include up to 30 parts by weight of a coumestan as a potentiator of the ability of the phytoestrogen to exert its effect on controlling the stimulation of estrogen production. The preferred coumestan is coumestrol. The preferred range of coumestan employed in the compositions is 20 to 30 parts by weight per 15 to 120 parts by weight of phytoestrogen.

Pantothenic acid, preferably employed as the calcium pantothenate, may be employed as an active ingredient, especially in the compositions used to treat an estrogen deficiency in post-menopausal females. The preferred dosage is 5 to 50 parts by weight per 15 to 120 parts by weight of the phytoestrogen.

One of the main uses of the new pharmaceutical compositions according to the present invention is in the treatment of disorders of female prepubescence up to menarche, the establishment of menstrual function. As explained in the background portion of this application when a female reaches puberty, she does not yet have the ability to produce adequate levels of estrogen because the ovaries are not fully developed yet. It often takes two to three years for the ovaries to fully develop and an adequate supply of estrogen prepared. A problem arises because at this stage in puberty there are inadequate positive and negative feedback mechanisms established between the hypothalamus, which produces the gonadotropin-releasing hormones, such as LRH and FSRH, the pituitary, which reacts to secretion by the hypothalamus of the LRH and FSRH to secrete LH and FSH, and the ovaries, which react to the pituitary's secretion of LH and FSH to produce estrogen. Some of the estrogen produced finds its way back to the hypothalamus and this serves as a negative feedback mechanism. The hypothalamus will respond to inadequate levels of estrogen, but secreting more gonadotropin-releasing hormones. The problem is that in a female not having yet reached menarche, this negative feedback mechanism will not help to produce more estrogen, and instead will result in a good deal of pain and discomfort.

The presently claimed compositions alter the negative feedback mechanism to signal the hypothalamus to secrete no more gonadotropin-releasing hormones. Thus the phytoestrogens of the present compositions exert an estrogen agonist effect or a weak estrogenic effect. A preferred composition for this purpose has the following formula:

(a) 15 to 45 parts by weight of one or more phytoestrogen compounds calculated as a free aglycon form of isoflavone;

(b) 20 to 50 parts by weight of Valerian root dry extract as a sedative;

(c) 10 parts by weight of beta-carotene;

(d) 15 to 25 parts by weight of pyridoxine hydrochloride;

(e) 12 to 25 parts by weight of Vitamin E;

(f) 100 parts by weight of calcium contained in a biologically acceptable calcium salt;

(g) 150 parts by weight of magnesium contained in a biologically acceptable magnesium salt;

(h) 10 to 25 parts by weight of zinc contained in a biologically acceptable zinc salt; and (i) up to 30 parts by weight of coumestan; in admixture with a biologically acceptable inert carrier.

Another important use of the compositions according to the present invention is in the control of PMS. The concentration of isoflavones in the PMS formula is preferably 45 to 50 mg per unit dose (calculated as the free aglycon form). The composition also contains an increased amount of magnesium (up to 200 mg as magnesium oxide), and Vitamin B6 (up to 50 mg). This unit dosage can itself be divided into two or three parts, and the female undergoing treatment can increase the dosage until there is relief of the PMS symptoms. However, it is best not to exceed an intake of 120 mg of isoflavones in a day.

It is best to administer the composition for treating PMS ten days before each menses is due. Once menses has arrived it is no longer necessary to continue administration of the composition. Alternatively, the female can take the medication on a regular basis with a progressive increase of isoflavone dosage during the last two weeks of the menstrual cycle.

The PMS formula is recommended for adult females with a regular menstrual cycle only. Any kind of disorder in the menstrual cycle of a premenopausal female contraindicates the taking of this medication. A preferred composition for the treatment of PMS is as follows:

(a) 45 to 120 parts by weight of one or more phytoestrogen compounds calculated as a free aglycon form of isoflavone;

(b) 55 to 75 parts by weight of dried licorice root;

(c) 50 to 80 parts by weight of Valerian root dry extract as a sedative;

(d) 20 parts by weight of beta-carotene;

(e) 30 to 50 parts by weight of pyridoxine hydrochloride;

(f) 15 to 30 parts by weight of Vitamin E;

(g) 200 parts by weight of calcium contained in a biologically acceptable calcium salt;

(h) 250 parts by weight of magnesium contained in a biologically acceptable magnesium salt;

(i) 15 to 50 parts by weight of zinc contained in a biologically acceptable zinc salt; and (j) up to 30 parts by weight of coumestan; in admixture with a biologically acceptable inert carrier.

When using the presently claimed compositions to treat PMS, the phytoestrogens therein are exerting an estrogen antagonistic effect. What is happening in PMS is that surges in estrogen production are occurring and it is these surges that result in the symptoms associated with PMS. Once again, alternation is needed in the negative feedback inhibition cycle. This time the hypothalamus is not able to fully read the high estrogen production that takes place at the ovaries. As a result the hypothalamus is still secreting gonadotropin-releasing hormones and the pituitary is still secreting the gonadotropic hormones which stimulate the ovaries into producing too much estrogen.

When the compositions according to the present are administered to a female with PMS, a correction takes place in the negative feedback inhibition. The phytoestrogens induce negative feedback from the hypothalamus which results in a slowing down of secretion of gonadotropic-releasing hormone. In turn less gonadotropic hormones are secreted by the pituitary and so the ovaries receive less stimulation to produce estrogen. As a result the oversupply of estrogen is reduced and the female suffering from PMS improves.

Yet another important feature of the present invention is the treatment of menopausal disorders. The preferred concentration of phytoestrogens in a daily dosage is 45 to 90 mg/day. In such a situation there is still a significant level of natural estrogen produced by the female's ovaries. Once again the daily dosage may be divided up into two or three doses. Because the sedative is an important component of the composition and has a limited duration, dividing the daily dosage up into three parts is highly advantageous. Even dividing the daily dosage into four or five parts may be considered.

When treating a female following menopause with an estrogen deficiency, the phytoestrogens in the compositions are functioning as estrogen agonists. Because too little estrogen is produced by the female's ovaries following menopause, the hypothalamus is receiving negative feedback. As a result more gonadotropin-releasing hormone is secreted and the pituitary in turn secretes more gonadotropic hormone. In turn the ovaries are stimulated to produce more estrogen. The problem is that after menopause the additional stimulation of the ovaries does not result in more estrogen production, but instead results in straining of the ovaries, the hypothalamus and the pituitary. When the present compositions are administered, the phytoestrogens contribute to the negative feedback received by the hypothalamus and the hypothalamus responds by producing less gonadotropin-releasing hormones. As a result the hypothalamus, pituitary and ovaries are all stabilized and the female's condition improves.

A preferred composition for the treatment of a female following menopause is as follows:

(a) 40 to 60 parts by weight of one or more phytoestrogen compounds calculated as a free aglycon form of isoflavone;

(b) 50 to 75 parts by weight of dried licorice root extract;

(c) 45 to 60 parts by weight of passion flower dry extract as a sedative;

(d) 20 parts of beta-carotene;

(e) 15 to 150 parts by weight of pyridoxine hydrochloride;

(f) 15 to 30 parts by weight of Vitamin E;

(g) 450 parts by weight of calcium contained in a biologically acceptable calcium salt;

(h) 250 parts by weight of magnesium contained in a biologically acceptable magnesium salt;

(i) 35 parts by weight of zinc contained in a biologically acceptable zinc salt;

(j) up to 30 parts by weight of coumestan; and (k) 5 to 50 parts by weight of pantothenic acid; in admixture with a biologically acceptable inert carrier.

The following examples represent non-limiting preferred features characteristic of the instant invention:

| EXAMPLE 1 (PREPUBESCENT COMPOSITION) | | |
|---|---|---|
| CONSTITUENTS | CHEMICALS | AMOUNT |
| Soybean phytoestrogens | Genistein, Daidzein, and their glycosides | 15 mg (Calculated as free |

EXAMPLE 1 (PREPUBESCENT COMPOSITION)

| CONSTITUENTS | CHEMICALS | AMOUNT |
|---|---|---|
| Valerian root | Valerian root dry extract | 20 mg (aglycon form) |
| Vitamin A | Beta-carotene | 10 mg |
| Vitamin B6 | Pyridoxine hydrochloride | 15 mg |
| Vitamin E | alpha-Tocopheryl acetate or succinate | 12 mg |
| Calcium | Calcium carbonate | 100 mg |
| Magnesium | Magnesium Oxide | 150 mg |
| Zinc | Zinc sulfate | 10 mg |

EXAMPLE 2 (PREPUBESCENT COMPOSITION)

| CONSTITUENTS | CHEMICALS | AMOUNT |
|---|---|---|
| Soybean phytoestrogens | Genistein, Daidzein, and their glycosides | 45 mg (Calculated as free aglycon form) |
| Valerian root | Valerian root dry extract | 50 mg |
| Vitamin A | Beta-carotene | 10 mg |
| Vitamin B6 | Pyridoxine hydrochloride | 25 mg |
| Vitamin E | alpha-Tocopheryl acetate or succinate | 25 mg |
| Calcium | Calcium carbonate | 100 mg |
| Magnesium | Magnesium Oxide | 150 mg |
| Zinc | Zinc sulfate | 25 mg |

EXAMPLE 3 (PMS COMPOSITION)

| CONSTITUENTS | CHEMICALS | AMOUNT |
|---|---|---|
| Soybean phytoestrogens | Genistein, Daidzein, and their glycosides | 45 mg (Calculated as free aglycon form) |
| Licorice Root | Deglycyrrhizinated root dry extract | 50 mg |
| Valerian root | Valerian root dry extract | 50 mg |
| Vitamin A | Beta-carotene | 20 mg |
| Vitamin B6 | Pyridoxine hydrochloride | 30 mg |
| Vitamin E | alpha-Tocopheryl acetate or succinate | 15 mg |
| Calcium | Calcium carbonate | 200 mg |
| Magnesium | Magnesium Oxide | 250 mg |
| Zinc | Zinc sulfate | 15 mg |

EXAMPLE 4 (PMS COMPOSITION)

| CONSTITUENTS | CHEMICALS | AMOUNT |
|---|---|---|
| Soybean phytoestrogens | Genistein, Daidzein, and their glycosides | 120 mg (Calculated as free aglycon form) |
| Licorice Root | Deglycyrrhizinated root dry extract | 75 mg |
| Valerian root | Valerian root dry extract | 80 mg |
| Vitamin A | Beta-carotene | 20 mg |
| Vitamin B6 | Pyridoxine hydrochloride | 50 mg |
| Vitamin E | alpha-Tocopheryl acetate or succinate | 30 mg |
| Calcium | Calcium carbonate | 200 mg |
| Magnesium | Magnesium Oxide | 250 mg |
| Zinc | Zinc sulfate | 50 mg |

Formula No. 5

(Menopausal Compound)

In menopause the estrogen deficiency demands the following two influences:

The estrogen supplying for improving functions of organs and tissues, and

The quieting of hypothalamus pituitary complex including vasomotor and thermoregulatory centers.

For this purpose it is necessary to potentiate the isoflavone activity and introduce into this formula the soybean phytoestrogen coumestrol. Its estrogenic activity is in 35 times more than isoflavones.

The other ingredients in this composition are called for alleviation of menopausal symptoms.

Vitamin B6 minimizes water retention, improves the function of central nervous system, and eases symptoms.

Magnesium relieves nervousness and irritability.

Pantothenic acid (Vitamin B5) is a powerful stress vitamin; helpful for adrenal function.

Passion flower is a source of mild sedative, relaxing and antidepressive compounds.

The daily dose of supplements in Example No 5 are:

| CONSTITUENTS | CHEMICALS | ACTIVE COMPOUND |
|---|---|---|
| Soybean phytoestrogens | Genistein, Daidzein, and their glycosides | 45 mg (Calculated as free aglycon form) |
| Coumestrol | Coumestan-related soybean phytoestrogen | 20 mg |
| Licorice root | Deglycyrrhizinated root dry extract | 50 mg |
| Passion-flower | Passiflora incarnata L., dry extract | 45 mg |
| Vitamin A | Beta-carotene | 20 mg |
| Vitamin B6 | Pyridoxine hydrochloride | 50 mg |
| Vitamine E | alpha-Tocopheryl acetate or succinate | 15 mg |
| Pantothenic Acid | Calcium Pantothenate | 5 mg |
| Calcium | Calcium carbonate | 450 mg |
| Magnesium | Magnesium Oxide | 250 mg |
| Zinc | Zinc sulfate | 35 mg |

Example 6

(Menopausal Composition)

The daily dose of ingredients in Example No 6 are:

| CONSTITUENTS | CHEMICALS | ACTIVE COMPOUND |
|---|---|---|
| Soybean phytoestrogens | Genistein, Daidzein, and their glycosides | 60 mg (Calculated as free aglycon form) |
| Coumestrol | Coumestan-related soybean phytoestrogen | 30 mg |
| Licorice root | Deglycyrrhizinated root dry extract | 75 mg |
| Passion-flower | Passiflora incarnata | 60 mg |

-continued

| CONSTITUENTS | CHEMICALS | ACTIVE COMPOUND |
|---|---|---|
| | L., dry extract | |
| Vitamin A | Beta-carotene | 20 mg |
| Vitamin B6 | Pyridoxine hydrochloride | 150 mg |
| Vitamine E | alpha-Tocopheryl acetate or succinate | 30 mg |
| Pantothenic Acid | Calcium Pantothenate | 50 mg |
| Calcium | Calcium carbonate | 450 mg |
| Magnesium | Magnesium Oxide | 250 mg |
| Zinc | Zinc sulfate | 35 mg |

What is claimed is:

1. A composition for controlling the stimulation of estrogen production, which comprises:
   (a) 15 to 120 parts by weight of one or more phytoestrogen compounds calculated as a free aglycon form of isoflavone;
   (b) up to 75 parts by weight of dried licorice root extract;
   (c) 10 to 80 parts by weight of a sedative selected from the group consisting of Valerian root dry extract, passion flower dry extract, and Ginseng root powder;
   (d) 10 to 50 parts by weight of beta-carotene;
   (e) 15 to 200 parts by weight of pyridoxine hydrochloride;
   (f) 12 to 50 parts by weight of Vitamin E;
   (g) 100 to 600 parts by weight of calcium contained in a biologically acceptable calcium salt;
   (h) 150 to 300 parts by weight of magnesium contained in a biologically acceptable magnesium salt;
   (i) 10 to 100 parts by weight of zinc contained in a biologically acceptable zinc salt;
   (j) up to 30 parts by weight of coumestan; and
   (k) up to 50 parts by weight of pantothenic acid; in admixture with a biologically acceptable inert carrier.

2. The composition for controlling the stimulation of estrogen production defined in claim 1 wherein the phytoestrogen is an isoflavone selected from the group consisting of genistein, daidzein, their glycosides and mixtures thereof.

3. The composition for controlling the stimulation of estrogen production defined in claim 1 wherein 20 to 30 parts by weight of the coumestan are contained in the composition and wherein the coumestan is coumestrol.

4. A method of controlling the stimulation of estrogen production in a female mammalian subject which comprises the step of administering to said mammal, a therapeutically effective amount of the composition defined in claim 1.

5. A composition for controlling the stimulation of estrogen production as defined in claim 1 which comprises:
   (a) 40 to 60 parts by weight of one or more phytoestrogen compounds calculated as a free aglycon form of isoflavone;
   (b) 50 to 75 parts by weight of dried licorice root extract;
   (c) 45 to 60 parts by weight of passion flower dry extract as a sedative;
   (d) 20 parts by weight of beta-carotene;
   (e) 15 to 150 parts by weight of pyridoxine hydrochloride;
   (f) 15 to 30 parts by weight of Vitamin E;
   (g) 450 parts by weight of calcium contained in a biologically acceptable calcium salt;
   (h) 250 parts by weight of magnesium contained in a biologically acceptable magnesium salt;
   (i) 35 parts by weight of zinc contained in a biologically acceptable zinc salt;
   (j) up to 30 parts by weight of coumestan; and
   (k) 5 to 50 parts by weight of pantothenic acid; in admixture with a biologically acceptable inert carrier.

6. A composition for controlling the stimulation of estrogen production which comprises:
   (a) 15 to 45 parts by weight of one or more phytoestrogen compounds calculated as a free aglycon form of isoflavone;
   (b) 20 to 50 parts by weight of Valerian root dry extract as a sedative;
   (c) 10 parts by weight of beta-carotene;
   (d) 15 to 25 parts by weight of pyridoxine hydrochloride;
   (e) 12 to 25 parts by weight of Vitamin E;
   (f) 100 parts by weight of calcium contained in a biologically acceptable calcium salt;
   (g) 150 parts by weight of magnesium contained in a biologically acceptable magnesium salt;
   (h) 10 to 25 parts by weight of zinc contained in a biologically acceptable zinc salt; and
   (i) up to 30 parts by weight of coumestan; in admixture with a biologically acceptable inert carrier.

7. A composition for controlling the stimulation of estrogen production which comprises:
   (a) 45 to 120 parts by weight of one or more phytoestrogen compounds calculated as a free aglycon form of isoflavone;
   (b) 55 to 75 parts by weight of dried licorice root;
   (c) 50 to 80 parts by weight of Valerian root dry extract as a sedative;
   (d) 20 parts by weight of beta-carotene;
   (e) 30 to 50 parts by weight of pyridoxine hydrochloride;
   (f) 15 to 30 parts by weight of Vitamin E;
   (g) 200 parts by weight of calcium contained in a biologically acceptable calcium salt;
   (h) 250 parts by weight of magnesium contained in a biologically acceptable magnesium salt;
   (i) 15 to 50 parts by weight of zinc contained in a biologically acceptable zinc salt; and
   (j) up to 30 parts by weight of coumestan; in admixture with a biologically acceptable inert carrier.

8. A method of treating a prepubescent female mammalian subject prior to menarch in need of control of stimulation of estrogen production which comprises the step of administering to said female mammalian subject, a therapeutically effective amount of the pharmaceutical composition defined in claim 5.

9. A method of treating a female mammalian subject for premenstrual syndrome by controlling the stimulation of estrogen production which comprises the step of administering to said female mammalian subject, a therapeutically effective amount of the composition defined in claim 7.

10. A method of treating a female mammalian subject for an estrogen deficiency following menopause, which comprises the step of administering to the subject in need of said treatment, a therapeutically effective amount of the composition defined in claim 5.

* * * * *